US005785679A

United States Patent [19]

Abolfathi et al.

[11] Patent Number: 5,785,679
[45] Date of Patent: Jul. 28, 1998

[54] METHODS AND APPARATUS FOR TREATING ANEURYSMS AND ARTERIO-VENOUS FISTULAS

[75] Inventors: Amir Abolfathi; Michael Hogendijk. both of Palo Alto; Farhad Khosravi. San Mateo, all of Calif.

[73] Assignee: Endotex Interventional Systems, Inc.. Menlo Park, Calif.

[21] Appl. No.: 504,293

[22] Filed: Jul. 19, 1995

[51] Int. Cl.[6] .................................................. A61M 31/00
[52] U.S. Cl. ........................... 604/51; 604/52; 604/53; 604/96; 604/101; 606/194
[58] Field of Search ................... 604/48–49, 51–53, 604/96, 99, 101–102, 104, 158, 164, 173, 264, 272, 280; 606/191–192, 194–195, 198; 623/1, 11, 12, 66; 128/898

[56] References Cited

U.S. PATENT DOCUMENTS

| 3,562,820 | 2/1971 | Braun . | |
|---|---|---|---|
| 3,991,767 | 11/1976 | Miller, Jr. et al. | 606/192 |
| 4,585,000 | 4/1986 | Hershenson . | |
| 4,708,718 | 11/1987 | Daniels | 604/53 |
| 4,909,252 | 3/1990 | Goldberger | 606/194 |
| 5,002,531 | 3/1991 | Bonzel | 604/96 |
| 5,100,429 | 3/1992 | Sinofsky et al. | 623/1 |
| 5,207,695 | 5/1993 | Trout, III | 606/191 |
| 5,213,577 | 5/1993 | Kratzer | 604/101 |
| 5,222,974 | 6/1993 | Kensey et al. | 606/213 |
| 5,261,875 | 11/1993 | Spears | 604/24 |
| 5,304,121 | 4/1994 | Sahatjian | 604/53 |
| 5,318,531 | 6/1994 | Leone | 604/101 |
| 5,328,471 | 7/1994 | Slepian | 604/101 |
| 5,342,301 | 8/1994 | Saab | 604/101 |
| 5,443,495 | 8/1995 | Buscemi et al. | 606/191 |
| 5,456,712 | 10/1995 | Maginot | 623/1 |
| 5,507,769 | 4/1996 | Marin et al. | 604/104 |
| 5,522,880 | 6/1996 | Barone et al. | 606/195 |
| 5,562,726 | 10/1996 | Chuter | 606/194 |
| 5,591,229 | 1/1997 | Parodi | 606/195 |

FOREIGN PATENT DOCUMENTS

WO 95/08289  3/1995  WIPO .

OTHER PUBLICATIONS

"Coil Case Reports—Utilization of Fibered Platinum Coils". Target Theurapetics, Inc., circa 1995.
"Responsive Hydrogels For Medical Uses", product brochure, Gel Med, Inc. Feb. 1994.
"Dispatch Coronary Infusion Catheter," product brochure, SciMed Life Sciences, Inc., 1994.
T. Chuter, C. Donayre and R. White, *Endoluminal Vascular Protheses*, pp. 21–35 and 217–235, Little Brown & Co. (1995).

*Primary Examiner*—Ronald K. Stright Jr.
*Attorney, Agent, or Firm*—Fish & Neave; Nicola A. Pisano

[57] ABSTRACT

Methods and apparatus are provided for temporarily excluding an aneurysm or an arterio-venous fistula from a flow path by transluminally disposing a hollow balloon catheter structure within the aneurysm so that its proximal and distal ends extend past the aneurysm while maintaining continuity of the flow path, and then injecting a synthetic molding material or a biological hardening agent into the aneurysm cavity to cause solidification of the volume within the cavity. Once the material within the excluded aneurysm has solidified, the balloon catheter structure is deflated and removed, so that the hardened mass forms a new lining for the organ or vessel, and relieves the weakened tissue of the aneurysm or fistula from further flow-induced stress.

9 Claims, 7 Drawing Sheets

METHODS AND APPARATUS FOR TREATING ANEURYSMS AND ARTERIO-VENOUS FISTULAS

FIELD OF THE INVENTION

The present invention relates generally to non-invasive techniques for repairing aneurysms occurring in hollow-body biological organs and vessels, for example, the aorta and iliac arteries, and arterio-venous fistulas. More particularly, the present invention relates to methods and apparatus for repairing aneurysms and fistulas using hardening agents that exclude the weakened tissue from a flow path.

BACKGROUND OF THE INVENTION

In recent years a number of non-invasive techniques have been developed to repair aneurysms occurring in hollow-body biological organs and vessels, for example, the aorta, using stent-graft techniques. These techniques generally seek to "re-line" the blood flow path through the organ, for example, by fixing a fabric material across the section of weakened tissue. The fabric is then held in place with one or more stents, which may be implanted, for example, using a balloon catheter. Such arrangements are described, for example, in Parodi U.S. Pat. No. 5,219,355 and European Application No. 0 461 791.

Such methods and apparatus are suitable for use in only a limited number of aneurysm situations, however. In particular, for such previously known methods to be effective, the portions of the organ proximal and distal to the aneurysm (i.e., the proximal neck and the distal cuff of the aneurysm) must be relatively straight to permit the stents and liner to obtain sufficient apposition on the organ or vessel walls.

Moreover, for such previously known methods to be effective, it is important that the nondilated diameter of the aorta proximal to the aneurysm be the same (within a few millimeters) of the nondilated portion of the distal cuff. Otherwise, the stent or stents selected to fasten the ends of the liner to the proximal and distal regions of the nondilated aorta may be incapable of the range of diametral expansion needed to engage both the proximal and distal regions.

If either of the above-described conditions occur, i.e., either insufficient lengths of the proximal neck and/or distal cuff, or large diametral discrepancies between those regions, there may be leakage at either or both of the proximal and distal ends of the graft. Consequently, the aneurysm may remain subjected to flow-induced pressure, with concomitant risk of rupture. These drawbacks of previously known non-invasive stent graft techniques are described by T. Chuter et al. in *Endoluminal Vascular Prostheses*, Little Brown & Co. (1995), Chapter 2 at pp. 23-33, which is incorporated herein by reference.

As further described in the foregoing text, while complicated bifurcated endovascular grafts may be used in those cases where the distal cuff is insufficiently long, use of such previously known grafts is limited to those situations where there is no aneurysm of the iliac arteries. See, for example, Chapter 4 of the foregoing text, which is incorporated herein by reference, especially at pp. 57-59 discussing patient selection criteria. Moreover, the use of bifurcated grafts, while increasing the number of candidates for non-invasive procedures, raises additional issues of graft sizing.

In addition to the restriction of previously known methods and apparatus mostly to those cases where some nondilated length of the aorta and/or distal cuff remains, the occurrence of aneurysms in organs and vessels other than the aorta, for example, in the iliac arteries, is untreatable using previously known non-invasive techniques.

While certain techniques have been recently developed for defining a cavity within an aneurysm and then filling the cavity with a heat activated molding material, as described, for example, in International Application PCT/US94/09837, these techniques do not provide for continuity of the flow path during the treatment period. Techniques such as described in the foregoing International Application therefore do not appear suitable for use in vascular aneurysms or in other applications where the flow path must remain uninterrupted.

In view of the foregoing, it would be desirable to provide non-invasive methods and apparatus suitable for repairing aneurysms that can be used in patients having relatively short lengths of nondilated aorta above the aneurysm, with little or no distal cuff length.

It further would be desirable to provide non-invasive methods and apparatus suitable for repairing aneurysms having large changes in diameter in the nondilated aorta regions proximal and distal to the aneurysm.

It also would be desirable to provide non-invasive methods and apparatus suitable for repairing aneurysms in hollow-body organs and vessels other than the aorta, for example, in the iliac arteries, and for repairing arterio-venous fistulas.

It would be yet further desirable to provide non-invasive methods and apparatus suitable for treating aneurysms in hollow-body organs and vessels so as to exclude the aneurysm entirely from either the hemodynamic circuit in the vascular system or other biological fluids or materials flowing through hollow-body organs of a nonvascular nature, so as to prevent leakage flow to the weakened aneurysm tissue, and thereby reduce the risk of rupture.

SUMMARY OF THE INVENTION

In view of the foregoing, it is an object of this invention to provide non-invasive methods and apparatus suitable for repairing aneurysms in hollow-body organs and vessels defining a flow path that can be used in patients having relatively short lengths of nondilated organ above the aneurysm neck, and little or no distal cuff length, while retaining continuity of the flow path.

It is a further object of the present invention to provide non-invasive methods and apparatus suitable for repairing aneurysms in hollow-body organs and vessels having large changes in diameter in the nondilated organ or vessel regions proximal and distal to the aneurysm.

It is another object of this invention to provide non-invasive methods and apparatus suitable for repairing aneurysms in hollow-body organs and vessels other the aorta, for example, in the iliac arteries, and for repairing arterio-venous fistulas. The methods and apparatus of the present invention also find applicability in gastro-intestinal, respiratory, reproductive organ, urethral applications and elsewhere where is desirable to "reline" a hollow-body organ and vessels.

It is yet another object of this invention to provide non-invasive methods and apparatus suitable for treating aneurysms in hollow-body organs and vessels so as to exclude the aneurysm entirely from, for example, the hemodynamic circuit, so as to prevent leakage flow to the weakened aneurysm tissue, and thereby reduce the risk of rupture.

These and other objects of the invention are accomplished in accordance with the principles of the invention by providing methods and apparatus for temporarily excluding an aneurysm from a flow path, for example, the blood flow path in the vascular system, while maintaining continuity of the flow path. A substance, such as a molding material or a hardening agent, is then injected into the aneurysm cavity. The injected substance causes, for example, thrombosis of the blood located within the cavity, or solidifies in response to exposure to an aqueous solution (e.g., blood) present in the cavity or in response to the application of heat.

In accordance with the invention, a hollow balloon catheter structure or other means of temporarily excluding flow from the aneurysm cavity, while providing uninterrupted flow through a main lumen, is transluminally disposed within the aneurysm so that its proximal and distal ends extend past the aneurysm. The balloon catheter structure is dimensioned to isolate the aneurysm cavity from the blood flow path, while permitting blood flow to pass through a lumen in the structure uninterrupted. A suitable molding material, for example, a hydrogel or polymer of a resorbable or permanent nature, a blood hardening agent, for example, fibrin or a tissue material, for example, collagen, is then injected into the aneurysm cavity, either by a catheter, laparoscopically, or by invasive surgical means.

Once the molding material has hardened, for example, either by inducing thrombosis of blood captured within the cavity or by body-temperature activation of the injected substance itself or other means for activation of the injected substance, the balloon catheter structure is deflated and removed. The hardened mass of thrombus or polymer thus forms the new lining of the organ, and relieves the weakened tissue of the aneurysm from further fluid flow stress.

In accordance with alternative embodiments of the present invention, aneurysms in the iliac arteries may also be treated using a combination of hollow balloon catheter and conventional catheter which are abutted against one another to form a mold for the new inner lining of the organ. That new inner liner is again formed by introducing a molding material or hardening agent into the cavity, defined by the walls of the aneurysm, the hollow balloon catheter and the conventional balloon catheter, to produce a coherent thrombsis or molded mass.

In yet further alternative embodiments, a wire mesh member may be disposed on the exterior surface of the hollow balloon catheter structure to serve as a framework for retaining the coherency of the thrombus formed by introduction of the hardening agent or molding material.

Further features of the invention, its nature and various advantages will be more apparent from the accompanying drawings and the following detailed description of the preferred embodiments.

DETAILED DESCRIPTION OF THE PREFERRED EMBODIMENTS

The present invention provides entirely new methods and apparatus for treatment of aneurysms occurring in hollow-body organs or vessels that overcome the limitations of previously known non-invasive methods. In particular, the methods and apparatus of the present invention permit an aneurysm to be isolated from flow-induced stress or other pressure by forming a solid mass of thrombus or molding material that serves as a new lining for the organ or vessel, while relieving flow-induced stresses in the weakened tissue of the aneurysm. During treatment, flow path across the aneurysm remains uninterrupted.

Figure 1:
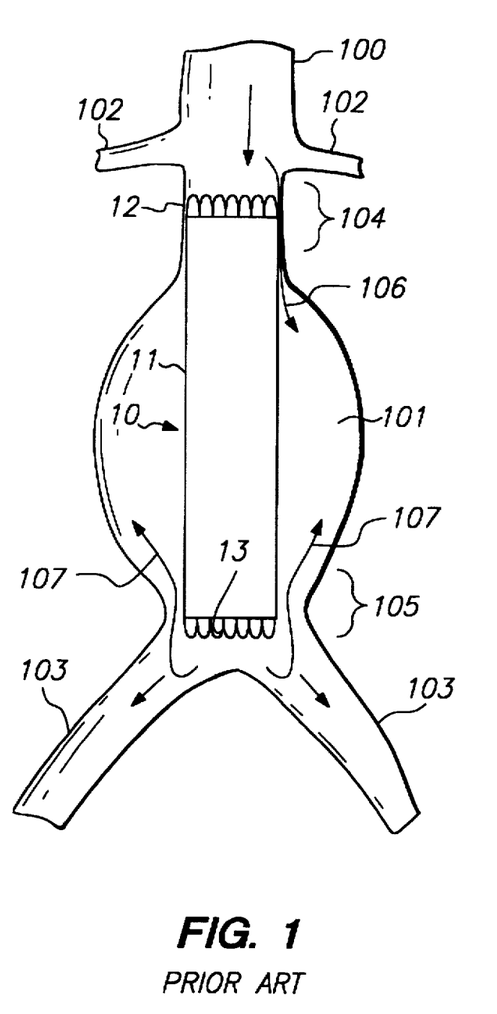
FIG. 1 is a elevation view, partly in section, of an abdominal aorta having implanted within it a previously known stent graft.

Referring to FIG. 1, a previously known stent graft arrangement, such as described in Parodi U.S. Pat. No. 5,219,355 and European Application No. 0 461 791, is described. As illustratively shown in FIG. 1, stent graft 10 is disposed across the region of the aneurysm 101 in aorta 100, which is located between renal arteries 102 and iliac arteries 103. Aneurysm 101 includes a proximal nondilated region of aorta 100 above the aneurysm referred to as "proximal neck" 104, and a distal region just above the bifurcation for iliac arteries 103 referred to as "distal cuff" 105.

Stent graft 10 generally includes a knitted graft liner 11, constructed for example, of Dacron®, that is integrated with stents 12 and 13 at either end. Stent graft 10 is generally threaded through a femoral artery using a delivery system that is per se known. Once stent graft 10 is positioned across aneurysm 101, as determined, for example, by radiography, stents 12 and 13 at the ends of the graft are deployed to anchor stent graft 10 to the nondilated portions of the aorta at proximal neck 104 and distal cuff 105.

As described briefly hereinabove, and in greater detail by T. Chuter et al. in *Endoluminal Vascular Prostheses*, Little Brown & Co. (1995), Chapter 2 at pp. 23–33, which is incorporated herein by reference, stent graft 10 is suitable for use only in those patients in which the nondilated portions of proximal neck 104 and distal cuff 105 are sufficiently long to permit stents 12 and 13 to be adequately deployed. In addition, variations in the aorta diameter above and below the aneurysm may exceed the capability of previously known stent grafts to properly engage the non-dilated tissue at both the proximal and distal ends of the aneurysm.

Generally, if either of the above-described conditions occur more invasive surgical techniques must be employed to treat the aneurysm. If stent graft 10 were to be employed where either the proximal neck was too short (e.g. under 10 mm) or the distal cuff were too short or non-existent, proximal leakage path 106 and retrograde leakage path 107 would arise. Because flow paths 106 and 107 would continue to exert flow-induced pressure on the walls of aneurysm 101, risk of rupture of aneurysm 101 and the catastrophic consequences attending such a rupture would remain unabated by stent graft 10.

Figure 2:
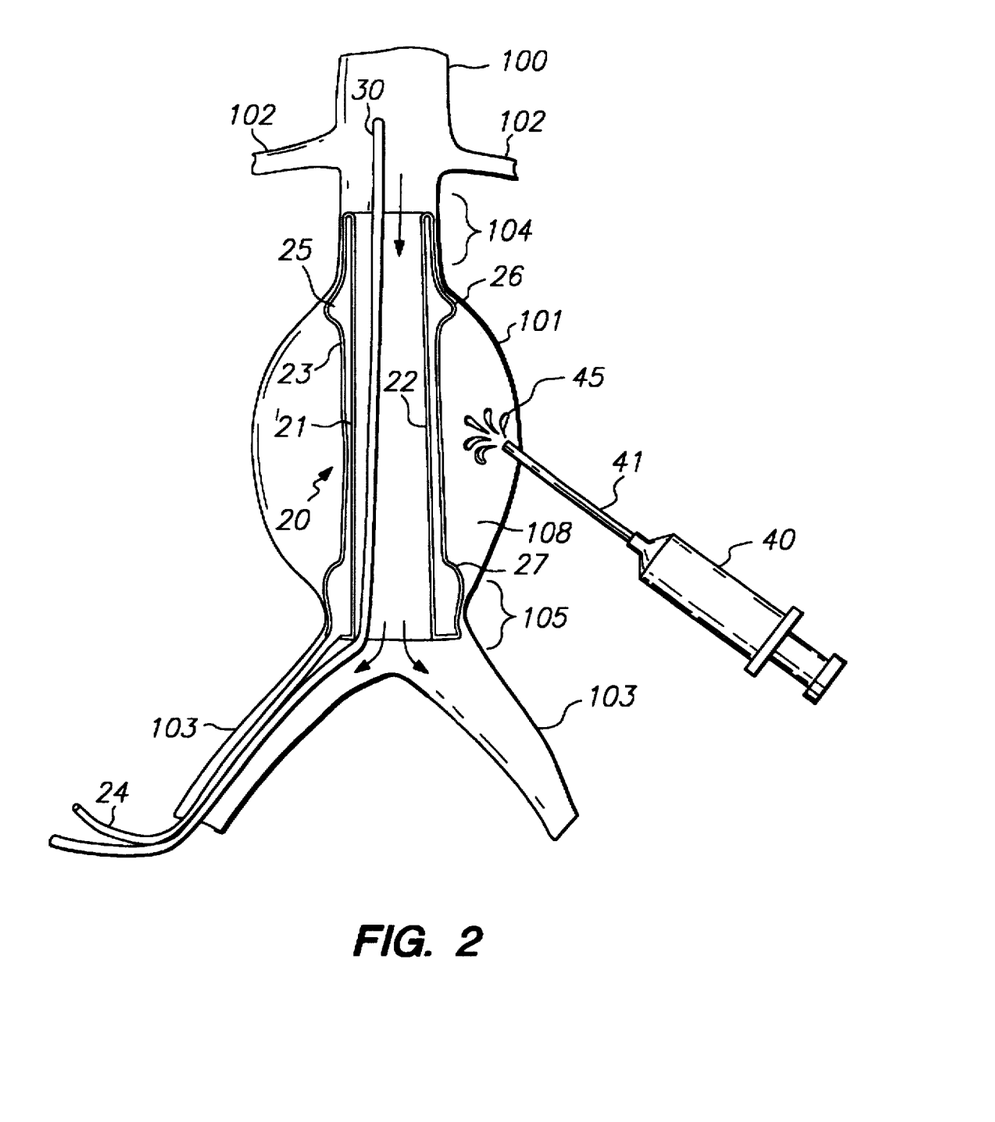
FIG. 2 is an elevation sectional view illustrating a first embodiment of the methods and apparatus of the present invention.

Referring now to FIG. 2, a first embodiment of the methods and apparatus of the present invention are described, in which like portions of aorta 100 are designated by like reference numerals. Apparatus constructed in accordance with the present invention is shown disposed across aneurysm 101 comprising hollow balloon catheter structure 20 disposed on guidewire 30.

Catheter structure 20 includes interior wall 21 forming central passageway 22, exterior wall 23, and lumen 24 for pressurizing cavity 25 formed by interior wall 21 and exterior wall 23. Catheter structure 20 may be formed of a suitably elastic material, such as polyester, polyethylene or polyvinyl chloride, and is delivered transluminally to the site of the aneurysm in a collapsed state under fluoroscopic guidance, as is typical for balloon catheters. Catheter structure 20 may include bands of suitable material to provide fluoroscopic contrast to assist in guiding the catheter structure to a desired location.

As will of course be understood by one of skill in the art of angioplasty catheter design, catheter structure 20 alternatively may have a mechanical structure formed of a tight woven metallic or polymeric structure, and thus include a mechanically expansible, rather than balloon inflated, deployed mechanism.

When deployed in aorta 100, blood flows freely through central passage 22 of catheter structure 20 to iliac arteries 103, while blood-filled cavity 108 is created between the walls of the aneurysm and the exterior wall 23 of catheter structure 20.

Catheter structure 20 may have a uniform outer diameter when inflated via lumen 24, or may include additional volumes of expandable material at the proximal and distal ends to form cuffs 26 and 27 as shown in FIG. 2. Cuffs 26 and 27 may be used to improve the seal between catheter structure 20 and proximal neck 104 and distal cuff 105 of aneurysm 101, respectively, so as to minimize communication between blood passing through central passage 22 and the volume captured in cavity 108.

Catheter structure 20 may be constructed with exterior wall 23 of a compliant material so as to conform to the anatomy of the proximal neck and distal cuff, and a less compliant, but pliable material along interior wall 22, for example, by controlling the density of the material used to construct catheter structure 20 during the manufacturing process.

Figure 3:
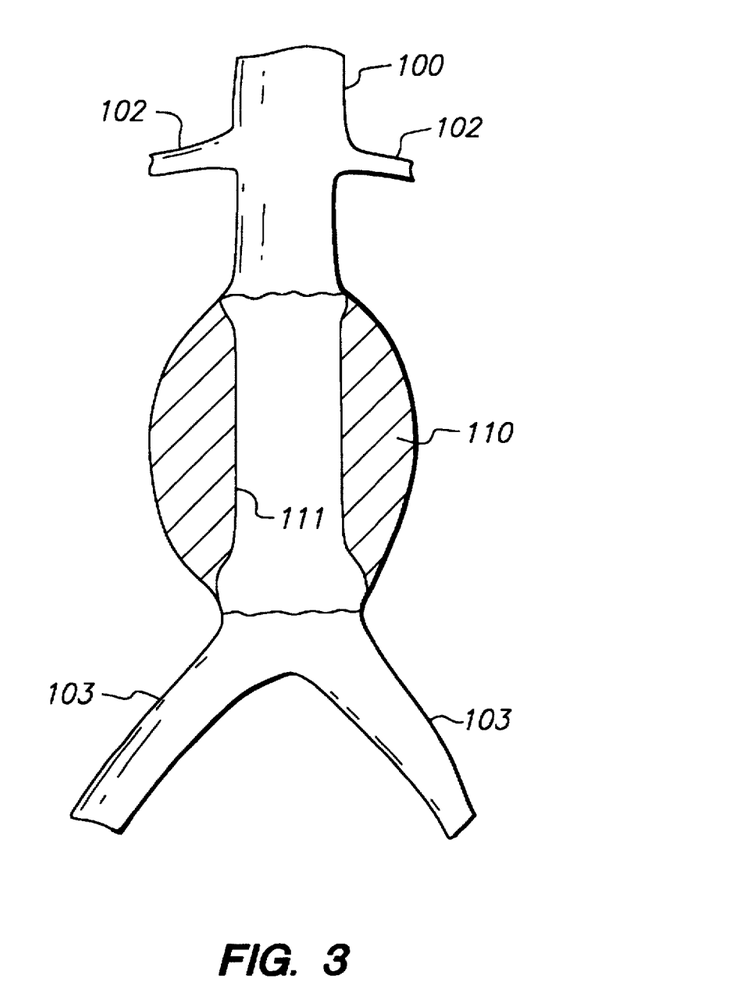
FIG. 3 is an elevational sectional view of a molded mass forming the relined inner surface of an aneurysm.

Still referring to FIG. 2, injection device 40 includes needle 41 that enters cavity 108 of aneurysm 101 either surgically or under laparoscopic guidance. If inserted laparoscopically, needle 41 may thus be introduced to the region of aneurysm 101 via a conventional trocar tube. In accordance with the present invention, injection device 40 delivers into cavity 108 substance 45, for example, a hardening agent or molding material (described below), that solidifies, or causes the blood captured in cavity 108 to solidify, into a coherent mass 110, as shown in FIG. 3.

Substance 45 may comprise a biological hardening agent, such as fibrin, that induces the blood captured in cavity 108 to form a coherent mass, or it may comprise a tissue material, such as collagen, which expands to fill the cavity. If fibrin is employed, it may be separated out of a sample of the patient's blood prior to the procedure to treat the aneurysm, and then injected into cavity 108 to cause thrombosis. On the other hand, collagen-based products, such as are available from Collatec, Inc., Plainsboro, N.J., may be used either to trigger thrombosis of the volume of blood in cavity 108, or for non-vascular organs or vessels, to fill cavity 108.

Alternatively, substance 45 may comprise a synthetic molding material, such as a starch-based poly ethylene glycol hydrogel or a polymer, such as poly-capro-lactone, that is heat hardenable or hydrophilic. In a preferred embodiment of the invention, a starch-based poly ethylene glycol hydrogel is used that swells when exposed to an aqueous solution. Hydrogels suitable for use with the present invention may be obtained, for example, from Gel Med, Inc., Bedford, Mass. Hydrogels or polymers may also be selected to harden, for example, upon exposure to body temperature or blood pH. In addition, catheter structure 20 may further include a resistively heated winding disposed on its outer surface (not shown) to activate hardening of substance 45.

As yet a still further alternative, substance 45 may comprise a composite of helical polyester and platinum fiber coils, such as available from Target Therapeutics, Inc., Fremont, Calif., that induce thrombosis of the blood within cavity 108.

Referring still to FIG. 2, substance 45 is injected into cavity 108 between aneurysm 101 and exterior wall 23 of catheter structure 20 so as to induce the blood captured in cavity 108 to form a coherent thrombotic mass, or in the case of synthetic molding materials, to entirely fill the cavity and form a solid mass. It is expected that, depending upon the type or hardening agent or molding material used, solidification of the content of cavity 108 of aneurysm 101 may take about ten minutes or less. The balloon of catheter structure 20 is then deflated, and the hollow balloon catheter structure 20 and guidewire 30 are withdrawn.

As shown in FIG. 3, the solidified mass formed in cavity 108 resulting from the addition of the hardening agent or molding material creates mass 110 having passageway 111. Passageway 111 becomes incorporated in the blood flow path upon removal of catheter structure 20. To facilitate removal of catheter structure 20 from solidified mass 110, exterior wall 23 of catheter structure 20 may be coated with a suitable adherent (i.e., non-stick) coating, for example, Teflon®, a registered trademark of the E.I. duPont de Nemours Company, Wilmington, Del. (polytetrafluorethylene), or other suitable biocompatible material, such as Parylene®, available from Paratech, Inc., Aliso Viejo, Calif.

Figure 4:
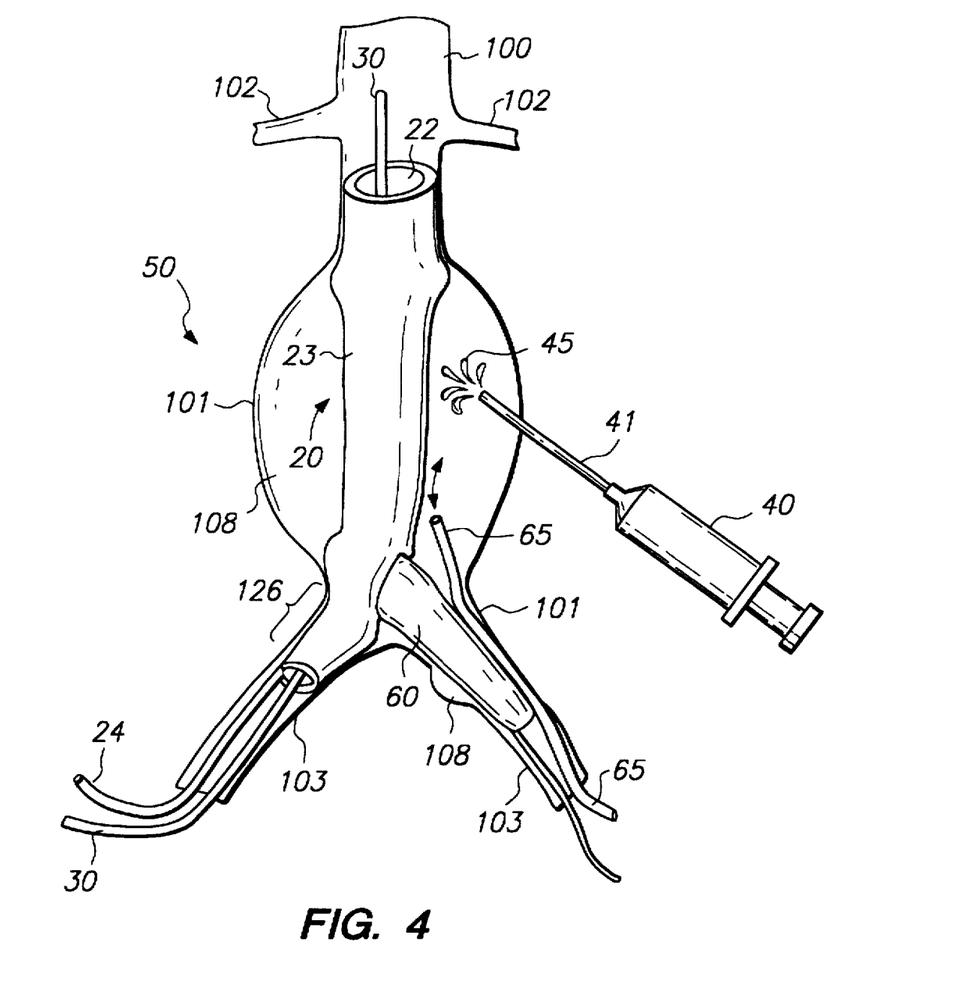
FIG. 4 is an elevation view, partly in section, of an alternative embodiment of the apparatus of the present invention for excluding an aneurysm that extends into the right branch of the iliac artery.

Referring now to FIG. 4, an alternative embodiment of the methods and apparatus of the present invention is described for use in situations where one or both external iliac arteries include aneurysms. In the embodiment of FIG. 4, like parts of the apparatus are again referenced with like numbers. Thus, apparatus 50 of the embodiment of FIG. 4 includes hollow balloon catheter structure 20, guidewire 30 and conventional balloon catheter 60 disposed in the right branch of the iliac artery and urged in abutment against the lower portion of catheter structure 20.

Catheter structure 20 includes an elastic outer membrane forming exterior wall 23 and includes a inner wall 21 forming passageway 22. Catheter structure 20 is mounted for deployment along guidewire 30 from a collapsed state in which it is delivered to the site of the aneurysm via a femoral artery. Unlike the hollow balloon catheter structure of FIG. 2, catheter structure 20 of FIG. 4 includes tapered lower portion 126 that extends into the left iliac artery.

Balloon catheter 60 may be of conventional balloon catheter construction and is delivered transluminally in a collapsed state into the right iliac artery via the corresponding femoral artery. In accordance with the present invention, balloon catheter 60 is delivered under fluoroscopic guidance to a location at which its distal end abuts against catheter structure 20. So long as completion of the treatment (i.e., injection and hardening of the cavity volume) is completed within about ten minutes or less, temporary blockage of blood flow in the iliac artery containing the conventional balloon catheter is not expected to cause any adverse effects.

Injection device 40 may then be positioned laparoscopically to inject substance 45 into cavity 108 defined by the walls of aneurysm 101 and the exterior walls of catheter structure 20 and balloon catheter 60. Substance 45, which again may be a hardening agent or molding material as described hereinabove, is then injected into cavity 108 to solidify the blood captured in cavity 108 into a coherent mass. Catheter structure 20 and balloon catheter 60 are then deflated and withdrawn, restoring blood flow to the iliac bifurcation via the new passages created in the solidified mass 110, similar to mass 110 of FIG. 3.

Alternatively, or in addition to injection device 40, catheter 65, which may be a multi-lumen catheter, may be employed as shown in FIG. 4. Catheter 65 is positioned with its distal end located in cavity 108 prior to inflation of balloon catheter 60, and may be used to inject substance 45 into cavity 108 instead of injection device 40 and needle 41. Catheter 65 may also be used to aspirate part of the volume of cavity 108, and to replace a controlled amount of the aspirated material with an appropriate hardening agent or molding material, thereby reducing the size of the aneurysm from its untreated condition.

If catheter 65 is used in the above-described manner to aspirate cavity 108 of aneurysm 101 prior to solidification of the contents of cavity 108, the excess tissue of the shrunken aneurysm may then be laparoscopically or surgically stapled, thus permanently reducing the size of the aneurysm and relieving pressure from the aneurysm on adjacent organs.

As will of course be apparent to one of skill in the art from the foregoing description, catheter 65 may be used with equal ease and to produce similar results with the embodiment of FIG. 2, either alternatively or in addition to injection device 40.

Figure 5:
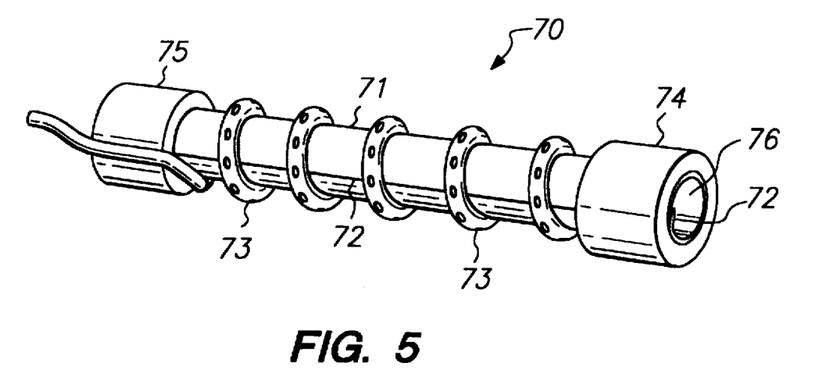
FIG. 5 is a perspective view of the aneurysm exclusion/injection portion of an alternative embodiment of an apparatus constructed in accordance with the present invention.
Figure 6:
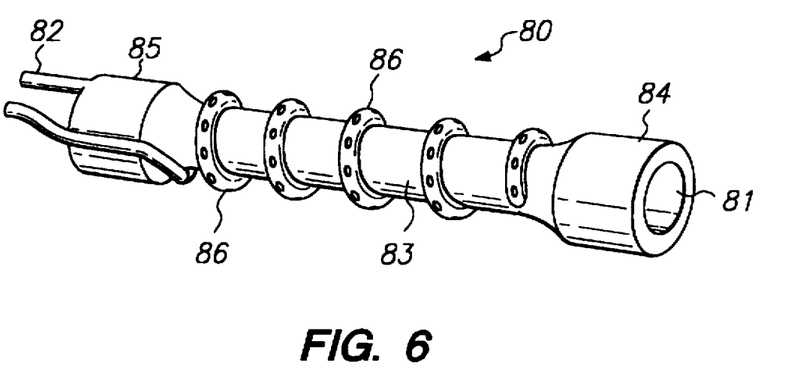
FIG. 6 is a perspective view of an alternative embodiment of the apparatus of FIG. 5.

With respect to FIGS. 5 and 6, the distal ends of two further alternative embodiments of the apparatus of the present invention are described. Only the balloon catheter elements of the apparatus are illustrated in FIGS. 5 and 6, since the proximal ends of the catheters, including the stop-cock and guidewire arrangements, are well-known to those of skill in the art of balloon angioplasty and catheter design.

Referring to FIG. 5, an alternative configuration to hollow balloon catheter structure 20 of FIG. 2 is described. Balloon apparatus 70 includes rolled sheet 71 having overlapping edges 72, and spiral porous balloon 73 wrapped along the length of rolled sheet 71. Cuff mechanisms 74 and 75, which may be inflatable, are disposed at the proximal and distal ends of balloon apparatus 70, and may be inflated by a non-porous lumen of spiral balloon 73 specifically connected to cuffs 74 and 75.

As described below, balloon apparatus performs the functions of not only catheter structure 20 of FIG. 2 (by providing a mold for solidification of the aneurysm cavity), but also provides the functions of injection device 40 (or catheter 65), as described hereinabove. Rolled sheet 71 may comprise a polyurethane material, while cuff mechanisms 74 and 75 may comprise a suitable elastic material, for example, poly vinyl chloride. Alternatively, cuff mechanisms 74 and 75 may employ a suitable mechanically expansible (non-inflatable) arrangement, and appropriate means for actuating such an arrangement.

In operation, balloon apparatus 70 is transluminally delivered to the site of the aneurysm under fluoroscopic guidance in a collapsed state. In its collapsed state, rolled sheet 71 is wound snugly against the delivery catheter, and spiral porous balloon 73 and cuff mechanisms 74 and 75 are likewise collapsed against the rolled sheet 71. Once located in position within the aneurysm, so that cuff mechanisms 74 and 75 are disposed adjacent to the proximal neck and distal cuff (or iliac bifurcation), respectively, cuffs 74 and 75 are actuated to exclude the aneurysm from communication with central passage 76 within rolled sheet 71.

As will of course be understood, actuation of cuff mechanisms 74 and 75 will cause rolled 71 sheet to unroll slightly and attain a larger internal diameter, while overlapping edges 72 prevent blood captured in the cavity (defined by the exterior of balloon apparatus 70 and the walls of the excluded aneurysm) from communicating with blood flowing through central passage 76.

Once apparatus 70 is disposed across the aneurysm and cuff mechanisms 74 and 75 deployed, the hardening agent or molding material, as described hereinabove, is injected into the cavity between the aneurysm and the outer surface of rolled sheet 71 via spiral porous balloon 73. When the mass of blood or molding material has solidified into a coherent mass, cuffs 74 and 75, and porous spiral balloon 73 are deflated and withdrawn. To facilitate deflation and withdrawal of apparatus 70 from the solidified mass formed in the aneurysm, the outer surfaces of apparatus 70 may be coated with Teflon® or other suitable biologically compatible non-stick material.

Referring now to FIG. 6, a further alternative embodiment of balloon apparatus 70 of FIG. 5 is described. Balloon apparatus 80 comprises a hollow balloon catheter structure as described with respect to FIG. 2 on which a spiral porous balloon is mounted, as for the embodiment of FIG. 5. In particular, balloon apparatus 80 includes interior passage 81, pressurizing lumen 82 and inflatable exterior surface 83 (which may have a uniform outer diameter or include proximal and distal cuffs 84 and 85), and spiral porous balloon 86 through which the hardening agent or molding material is injected into the excluded aneurysm.

Operation of balloon apparatus of FIG. 6 is similar to that described above with respect to the embodiment of FIG. 5. Specifically, balloon apparatus 80 is first delivered transluminally to the site of the aneurysm under fluoroscopic guidance in a collapsed state. Balloon apparatus 80 is then pressurized via lumen 82 to exclude the aneurysm from the blood flow path while permitting continued flow through passage 81. A suitable hardening agent or molding material is then introduced into the cavity in the aneurysm via porous spiral balloon. Once the mass in the aneurysm is solidified, balloon apparatus 80 is then deflated and withdrawn, again leaving a "relined" aneurysm passage similar to that shown in FIG. 3.

Figure 7:
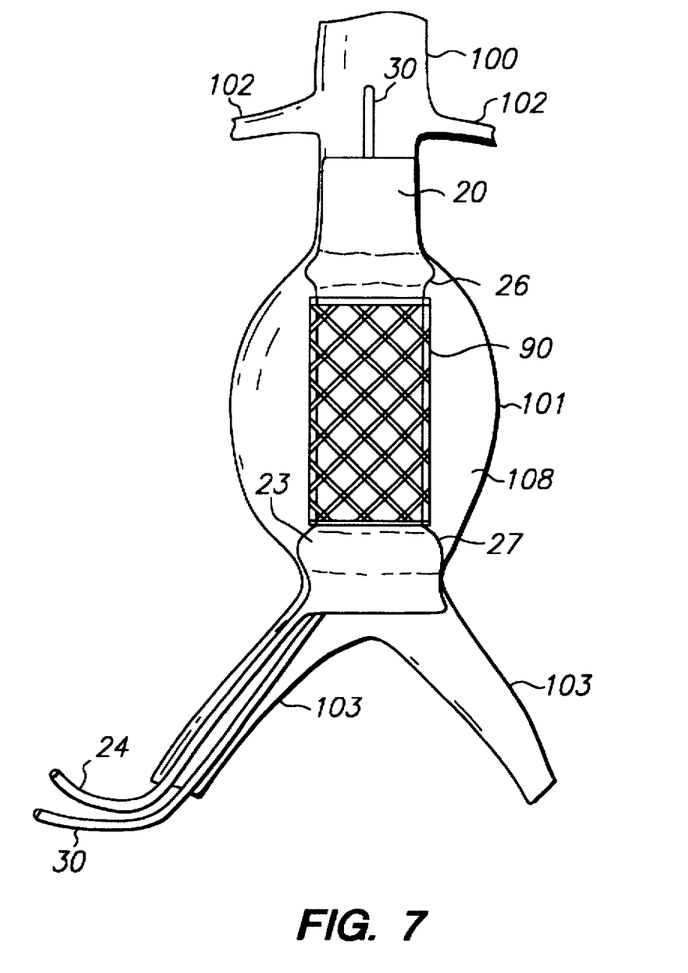
FIG. 7 is an elevational view of a mesh member disposed on the apparatus of FIG. 2.
Figure 8:
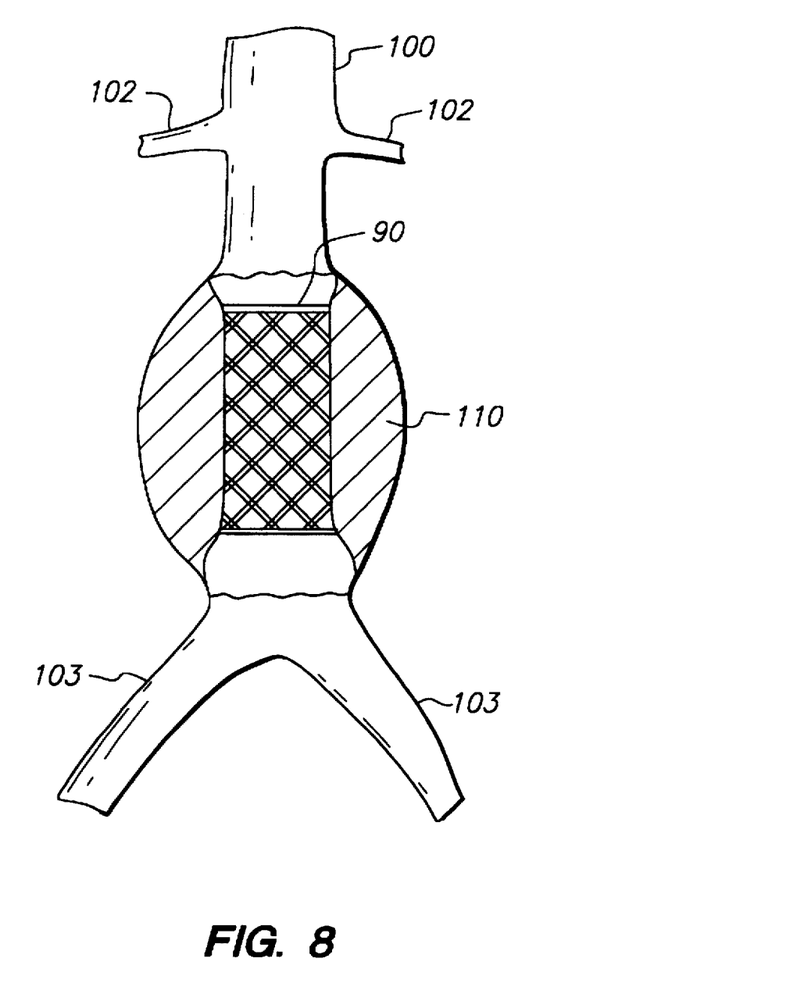
FIG. 8 is a sectional view similar to that of FIG. 3, showing the mesh member of FIG. 7 integrated with the molded mass formed within the aneurysm.

With respect to FIGS. 7 and 8, an exemplary configuration of mesh 90 for use with the catheter structure of FIG. 2 is described. Mesh 90 comprises a thin wire or polymeric net or mesh disposed around the exterior wall 23 of hollow balloon catheter structure 20. Mesh 90 is placed around catheter structure 20 prior to delivery of catheter structure 20 transluminally to the aneurysm site, and may be self-expanding or expanded by inflation of catheter structure 20.

When the molding material or hardening agent is introduced into cavity 108 of aneurysm 101, mesh 90 becomes incorporated into the solidifying mass 110 (see FIG. 8), and is expected to reduce embolization of the molding material or hardening agent, and thus reduce the risk of thrombosis downstream from mass 110. Upon completion of the hardening of the volume of cavity 108, hollow balloon catheter structure 20 is deflated, and mesh 90 is left in position within the aneurysm, where it forms part of the relined passage of the aorta.

It will of course be understood by those skilled in the relevant arts that the exemplary embodiments of the invention described hereinabove in no way limit the intended use of the methods and apparatus of the present invention, and that the methods of the present invention could be implemented using catheter structures having other configurations.

In addition, while the methods and apparatus of the present invention have been described with reference to excluding aneurysms occurring in the abdominal aorta, the methods and apparatus of the present invention are equally applicable to gastrointestinal, respiratory, reproductive organ, urethral applications and elsewhere where is desirable to "reline" a hollow-body organ or vessel.

Thus, for example, the methods and apparatus of the present invention may be used to treat arterio-venous fistulas in a manner similar to that described above for the aorta. Application of the present invention in such treatment is consistent with the use of previously-known stent-graft techniques in treatment of such fistulas, as described, for example, in the above-mentioned T. Chuter et al. text, *Endoluminal Vascular Prostheses*, at Chapter 10 at pp. 217-235, which is incorporated herein by reference. The methods and apparatus of the present invention are expected to provide even greater flexibility in the treatment of such abnormalities.

While preferred illustrative embodiments of the present invention are described above, it will be obvious to one skilled in the art that various changes and modifications may be made therein without departing from the invention and it is intended in the appended claims to cover all such changes and modifications which fall within the true spirit and scope of the invention.

What is claimed is:

1. A method of treating an aneurysm in a hollow-body organ or vessel defining a flow path, the method comprising steps of:

providing a tubular member having an exterior surface and first and second ends, a portion of the tubular member defining a lumen having an inlet for the flow path at the first end and an outlet for the flow path at the second end, each of the first and second ends including an inflatable cuff, the tubular member having a contracted state permitting transluminal delivery, wherein the lumen has a first diameter and the inflatable cuffs are deflated, and a deployed state, wherein the lumen has a second diameter, larger than the first diameter, to provide continuity of the flow path and the inflatable cuffs are inflated so that the exterior surface and inflatable cuffs exclude the aneurysm from the flow path;

transluminally delivering the tubular member to a position extending across the aneurysm;

inflating the inflatable cuffs so that the tubular member assumes its deployed state to exclude the aneurysm from communicating with the flow path and to create a cavity defined by the aneurysm, the inflatable cuffs and the exterior surface, the cavity containing biological material isolated from the flow path;

injecting a substance into the cavity to cause solidification of the biological material into a mass;

deflating the inflatable cuffs so that the tubular member returns to its contracted state; and withdrawing the tubular member from the aneurysm to create a first passageway through the mass, the first passageway being incorporated into the flow path.

2. The method of claim 1 wherein the tubular member comprises a unitary balloon structure to inflate said cuffs, the step of inflating the inflatable cuffs comprising inflating the balloon structure and said cuffs and the step of deflating the inflatable cuffs comprising deflating the balloon structure and said cuffs.

3. The method of claim 1 wherein the step of injecting a substance comprises a step of injecting a synthetic molding agent or a biological hardening agent.

4. The method of claim 1 further comprising steps of inserting a drainage catheter into the cavity and, prior to the step of injecting a substance, a step of aspirating a portion of the biological material from the cavity using the drainage catheter.

5. The method of claim 1 further comprising, before the step of injecting a substance into the cavity, steps of:

providing an injection device having a needle; and under laparoscopic guidance, inserting the injection device so that the needle enters the cavity.

6. The method of claim 1 wherein the step of providing a tubular member includes providing a tubular member comprising means for injecting a substance into the cavity, the step of injecting a substance into the cavity employing the means for injecting.

7. The method of claim 1 further comprising steps of:

providing a mesh member on an exterior surface of the tubular member;

disposing the mesh member within the cavity so that it is incorporated within the mass; and leaving the mesh member incorporated within the mass during the step of withdrawing the tubular member from the aneurysm.

8. The method of claim 1 wherein the hollow-body organ or vessel is an aorta, the aneurysm includes a portion of the aorta and a first iliac artery adjacent to the aorta, and the step of transluminally delivering the tubular member to a position across the aneurysm includes locating the tubular member so that it extends into a second iliac artery, the method further comprising, before the step of injecting a substance into the cavity, steps of:

transluminally delivering a balloon catheter into the first iliac artery so that a distal end of the balloon catheter is urged against a portion of the exterior surface of the tubular member;

inflating the balloon catheter while it is urged against the tubular member, so that the cavity is defined by the aneurysm, the inflatable cuffs, the exterior surface of the tubular member and the exterior surface of the balloon catheter; and after the step of injecting a substance into the cavity to cause solidification of the biological material into a mass, deflating and withdrawing the balloon catheter to create a second passageway through the mass, the second passageway having a first end communicating with the first passageway and a second end communicating with the first iliac artery, the second passageway also being incorporated into the flow path.

9. The method as defined in claim 1 wherein the step of delivering the tubular member is performed via an access artery.

* * * * *

UNITED STATES PATENT AND TRADEMARK OFFICE
CERTIFICATE OF CORRECTION

PATENT NO. : 5,785,679
DATED : July 28, 1998
INVENTOR(S) : Abolfathi et al.

It is certified that error appears in the above-identified patent and that said Letters Patent is hereby corrected as shown below:

Column 1,
Line 7, replace "non" with -- minimally --.
Line 17, replace "non" with -- minimally --.
Line 52, replace "non" with -- minimally --.
Line 64, replace "non" with -- minimally --.

Column 2,
Line 4, replace "non" with -- minimally --.
Line 16, replace "non" with -- minimally --.
Line 21, replace "non" with -- minimally --.
Line 24, replace "non" with -- minimally --.
Line 30, replace "non" with -- minimally --.
Line 41, replace "non" with -- minimally --.
Line 49, replace "non" with -- minimally --.
Lines 53-54, replace "non" with -- minimally --.
Line 55, after "other" insert -- than --.
Line 60, after "where" insert -- it --.
Line 63, replace "non" with -- minimally --.

Column 3,
Line 56, replace "a" with -- an --.

Column 4,
Line 17, replace "non" with -- minimally --.
Line 59, replace "were" with -- was --.

UNITED STATES PATENT AND TRADEMARK OFFICE
CERTIFICATE OF CORRECTION

PATENT NO. : 5,785,679
DATED : July 28, 1998
INVENTOR(S) : Abolfathi et al.

It is certified that error appears in the above-identified patent and that said Letters Patent is hereby corrected as shown below:

Column 6,
Line 17, replace "induce" with -- induces --.
Line 26, replace "or" (first occurrence) with -- of --.
Line 55, replace "a" with -- an --.

Column 9,
Line 19, after "where" insert -- it --.

Signed and Sealed this

Twelfth Day of March, 2002

*Attest:*

*Attesting Officer*

JAMES E. ROGAN
*Director of the United States Patent and Trademark Office*